United States Patent [19]

Widder et al.

[11] 4,345,588
[45] Aug. 24, 1982

[54] METHOD OF DELIVERING A THERAPEUTIC AGENT TO A TARGET CAPILLARY BED

[75] Inventors: Kenneth J. Widder, Carboro, N.C.; Andrew E. Senyei, Long Beach, Calif.

[73] Assignee: Northwestern University, Evanston, Ill.

[21] Appl. No.: 163,716

[22] Filed: Jun. 27, 1980

Related U.S. Application Data

[63] Continuation-in-part of Ser. No. 32,399, Apr. 23, 1979, and Ser. No. 859,842, Dec. 12, 1977, said Ser. No. 32,399, is a continuation-in-part of Ser. No. 820,812, Aug. 1, 1977, abandoned.

[51] Int. Cl.$^3$ ............................ A61K 9/50; A61K 9/38
[52] U.S. Cl. ................................. 128/1.3; 128/260; 252/62.53
[58] Field of Search .............................. 128/1.3, 260

[56] References Cited

U.S. PATENT DOCUMENTS

| | | | |
|---|---|---|---|
| 3,474,777 | 10/1969 | Figge et al. | 128/1.3 X |
| 3,663,687 | 5/1972 | Evans. | |
| 3,937,668 | 2/1976 | Zolle. | |
| 4,106,488 | 8/1978 | Gordon. | |
| 4,136,683 | 1/1979 | Gordon | 128/1.3 X |
| 4,147,767 | 4/1979 | Yapel. | |
| 4,247,406 | 1/1981 | Widder et al.. | |
| 4,269,826 | 5/1981 | Zimmermann et al.. | |

FOREIGN PATENT DOCUMENTS 4406 of 1874 United Kingdom ................ 128/260

OTHER PUBLICATIONS

Merck Index, entry 202.
Proceedings Nat'l. Academy of Science, vol. 72, No. 3, pp. 937–940, Mar. 1973, paper by Hahn, Braun et al.
Freeman et al., J. Appl. Physics., Suppl., vol. 31, No. 5, 4045–4055, (May, 1960).
Meyers et al., Amer. J. Roentg., 90, 1068–1077, (Nov. 1963).
Takai et al., Chem. Abs., vol. 80, No. 5, p. 293, Abstract 52392a, (1974).

*Primary Examiner*—Kyle L. Howell
*Assistant Examiner*—Nancy A. B. Swisher

[57] ABSTRACT

Intravascularly-administrable, magnetically-localizable biodegradable microspheres containing a therapeutic agent, such as an oncolytic agent, are prepared and administered so that they can be permanently localized in a target capillary bed for release of the therapeutic agent therein. The effects of the therapeutic agent can thereby be relatively confined to the area of the capillary bed. Of particular importance is the administration of oncolytic agents by the method, since this permits the undesirable side effects of the oncolytic agents to be substantially reduced, while at the same time increasing the anti-cancer effectiveness of the drug.

12 Claims, No Drawings

METHOD OF DELIVERING A THERAPEUTIC AGENT TO A TARGET CAPILLARY BED

CROSS-REFERENCES

This application is a continuation-in-part of co-pending application Ser. No. 032,399 filed Apr. 23, 1979, which is a continuation-in-part of application Ser. No. 820,812, filed Aug. 1, 1977, now abandoned. This application is also a continuation-in-part of co-pending application Ser. No. 859,842 filed Dec. 12, 1977.

BACKGROUND AND PRIOR ART

Specific delivery of chemotherapeutic agents to desired target sites with a minimum of systemic side effects constitutes one of the ongoing challenges of chemotherapy. Drugs administered parenterally have activity in areas of the body where activity is not desired. In 1974, Kramer proposed albumin microspheres as vehicles for achieving specificity in drug delivery. *J. Pharm. Sci.*, 63, 1646–1647 (Oct. 1974). Entrapment of the anti-cancer drug mercaptopurine was demonstrated but not specificity of delivery. Local compartmentalization of water soluble chemotherapeutic agents at desired target sites, if it could be achieved, would permit administration of much lower doses by largely eliminating systemic dilution of the drug. In addition, many of the adverse side effects that are often the result of systemic distribution could be eliminated. Unfortunately, prior to the present invention, no system of administration has been provided which can effectively deliver therapeutic agents intravascularly to a selected site.

Freeman et al proposed in 1960 that magnetic iron particles might be used as a means for transporting radiation or some healing chemical to a particular spot in the body, the particles being magnetically directed. *J. App. Phys.*, Supp. Vol. 31, 404S–405S (May 1960). It was suggested that the iron particles could be alloyed with the proper choice of radioactive element, or that they could be coated with an adsorbed layer of a therapeutic agent. Meyers et al also suggested the use of carbonyl iron particles as vehicles for site specific delivery of chemotherapeutic agents. *Amer. J. Roentg.*, 90, 1068–1077 (Nov. 1963). Magnetic iron particles of 1 to 3 microns in diameter were shown to be temporarily localized in the vessels or gastrointestinal tract of dogs with a magnetic field of approximately 5,000 gauss. The particles were removed by blood flow when the magnet was removed. However, it appeared that a few of the particles had been pulled through the artery into the tissues by the magnetic field, and remained there after removal of the magnetic field.

U.S. Pat. No. 3,474,779, granted Oct. 28, 1969, describes a method for administering therapeutic agents in which magnetic microspheres of a size up to 5 microns are intravascularly administered so that they pass into a capillary bed where they are caught by an applied magnetic field, and magnetically retained in the capillary bed until the therapeutic agent contained in the microspheres is released. It is proposed that this method can be used for administering anti-cancer drugs. No specific examples are given, and there is no suggestion that the microspheres would remain in the capillary bed after removal of the magnetic field.

It is known that the surface properties of magnetic particles, such as carbonyl iron, lead to irreversible intravascular clumping upon exposure to a magnetic field unless they are coated with electronegative polymer such as albumin. See Nakamura et al, *J. App. Phys.*, 42, 1320–1324 (1971); Alksne et al, *Surgery*, 60, 212 (1966); and Mosso et al, *Ann. Surg.*, 178:5, 633 (1973).

Takai et al proposed that magnetic materials coated with organic polymers could be used as carriers for drugs and x-ray contrast media, and that they could be localized in a desired area of the body by means of permanent magnet. Such a coated magnetic material was orally administered to a patient with peptic ulcers and localized on the lesions, which permitted sharper x-ray photos of the ulcers to be obtained. *Chemical Abstracts*, Vol. 80, No. 5, page 293, Abstract 52392a (1974).

Microcapsules containing magnetic particles are disclosed in U.S. Pat. No. 2,971,916. Microcapsules of 3 to 150 microns in diameter are formed by coacervation, the capsules having walls of hardened organic colloid material enclosing an oily liquid containing a dispersion of magnetic powder. No medical application is suggested, the capsules being indicated as useful for imprinting of data on record sheets.

U.S. Pat. No. 3,663,687, issued May 16, 1972, proposes the use of biodegradable microspheres for the intravascular administration of therapeutic agents. The microspheres are dimensioned so that they will lodge in the capillaries. The microspheres are dissolved by enzymatic action, thereby releasing the therapeutic agent. The examples disclose microspheres having sizes ranging from 10 to 50 microns. This patent further discloses that the rate of release of the therapeutic agent can be controlled by cross-linking of the protein material forming the microspheres, by either heat or chemical treatment.

U.S. Pat. No. 3,937,668, issued Feb. 10, 1976, describes a method for preparing albumin microspheres which can be used for delivery of therapeutic agents, among other uses. It is stated that the microspheres may range in size from 1 to 200 microns.

SUMMARY OF INVENTION

The present invention provides a novel method of delivering a therapeutic agent to a target capillary bed of the body. The method takes advantage of the difference in blood flow rates between arteries and capillaries. The magnetic microspheres used for administering the therapeutic agent are selectively localized in the target capillary bed by applying a magnetic field which immobilizes the microspheres at the much slower blood flow rate of the capillaries but not at the flow rate of the arteries into which the microspheres are initially introduced. Moveover, the magnetic field need be applied only for a short time, after which it can be removed. This is based on the discovery that microspheres of sufficiently small size can be permanently localized in the capillaries, once they have been magnetically attracted to the walls of the capillaries and immobilized thereon, even though the blood continues to flow through the capillary bed in a substantially normal manner. In other words, the immobilized microspheres do not plug-up or block the capillaries as described in the method of U.S. Pat. No. 3,663,687. Further, the continued application of the magnetic field until the drug has been released in the capillary bed is not required, as described in other prior art references cited above.

For effective magnetic control, the microspheres are introduced into an artery upstream of the capillary bed where they are to be localized, the selected capillary bed being associated with the target site. It is therefore of critical importance that the microspheres have a degree of magnetic responsiveness which permit them to pass through the arteries without significant holdup under the applied magnetic field while being immobilized and retained in the capillaries. The present invention achieves this objective by utilizing the difference in flow rates of the blood in the larger arteries and in the capillaries. In addition, the albumin surface prevents clump formation, thus allowing relatively normal blood perfusion at the area of retention. Prior to the present invention it has not been recognized or demonstrated that such discrimination in magnetic responsiveness could be obtained.

With respect to the circulatory system, mean flow velocity may be defined as the volume of blood flow through an artery, capillary, or vein divided by the cross-sectional area of the vessel. In large arteries, the velocity is of the order of 30 cm/sec, while in smaller arteries it may range from about 10 to 20 cm/sec. In veins, the flow capacity is of the order of 15 cm/sec. In contrast to the flow rates in veins and arteries, the blood flow rate in capillaries is of the order of 0.05 cm/sec. By means of a standardized test apparatus, it was demonstrated that with an ordinary permanent bipolar magnet producing a field of 8,000 gauss the difference in arterial and capillary flow rates could be used to achieve carrier retention at the desired flow of 0.05 cm/sec while permitting passage at higher flow rates. This permits the magnetic field to be applied at the time of the intra-arterial administration, assuring that the microspheres will be caught in the target capillary bed without at the same time immobilizing any substantial amount of the administered microspheres in the larger arteries. The microspheres carrying the therapeutic agent will therefore pass rapidly through the artery into which they are administered to the target capillary bed where they will be caught and retained, thereby effectively concentrating the agent at the target site. While being retained in the capillary bed, if desired, the applied magnetic field can be increased in strength, causing the microspheres of sufficiently small size to be drawn through the capillary walls into the tissue, and thereby retained at the target site after the magnetic field is removed.

Even without an increase in the strength of the magnetic field after immobilizing the microspheres in the capillary bed, it has been discovered that the microspheres can be substantially permanently immobilized therein. This is true even though the microspheres are of such a small size that they can pass readily through the capillary bed with the blood flowing therethrough. It appears that when the microspheres of such small size are attracted to the capillary walls by the applied magnetic force, that they adhered to the capillary walls and become permanently immobilized so that the magnetic field can be removed while leaving the microspheres with the therapeutic agent therein within the capillary bed. At the same time, substantially normal blood flow can continue through the capillary bed, including blood flow through the capillaries containing the microspheres.

With microspheres prepared in accordance with the present invention, at least 90% of the microspheres can be immobilized by a magnetic induction of 8,000 gauss when an aqueous suspension of the microspheres is pumped at a rate of 0.05 cm/sec through a conduit of 0.168 cm internal diameter, but not over 10% of the microspheres will be immobilized by the same magnetic induction when pumped through the conduit at a flow rate of 10 cm/sec or greater.

DETAILED DESCRIPTION

The matrix material for forming the microspheres is a biodegradable material such as an amino acid polymer. Other biodegradable materials include triglyceride fats or oils, or fatty acids derived therefrom, or carbohydrates. Such substances are biodegradable by proteolytic enzyme action. The biodegradable material should be usable as a matrix in which the magnetic particles can be imbedded with the therapeutic agent distributed there through, and it should be subject to degradation in capillaries or in the tissues surrounding capillaries, such as by enzymatic degradation.

For example, usable amino acid polymers include natural amino acids (proteins) and synthetic amino acid polymers. The preferred polymer is albumin, which may be animal or human albumin, but is preferably human serum albumin. Other water-soluble proteins such as hemoglobin can be substituted for albumin, the preference being for human hemoglobin. Usable synthetic amino acid polymers include poly-L-lysine and poly-L-glutamic acid. For example, a poly-L-lysine or poly-L-glutamic acid in the molecular weight range of 20,000–50,000 can be used alone or in combination with another polymer such as albumin. However, since human serum albumin is a nearly ideal material for the purpose of the present invention, there is no necessity to use other comparable amino acid polymers. At the same time, however, such amino acid polymers are within the scope of this invention, as are other biodegradable substances having the characteristics described above.

The magnetic particles include ferri- and ferro-magnetic compounds, such as magnetic iron oxides. The preferred magnetic particles are the black oxide or iron, magnetite ($Fe_3O_4$). Carbonyl iron of appropriate size can be used instead of the $Fe_3O_4$. It is important that the magnetic particles be in an ultra-fine state of subdivision. The magnetic particles should have an average size of not over 1,000 Angstroms, and preferably not over 300 Angstroms. Techniques are known for producing such extremely small size magnetic particles. These include fine grinding, vacuum deposition, and chemical precipitation. Fine grinding in a ball mill can be used to produce a colloidal suspension of magnetic particles. Commercially, fine powders or suspensions of $Fe_3O_4$ are available from Ferrofluidics Corporation, Burlington, Massachusetts. The size range of the particles is from 100 to 200 Angstroms. Aqueous base suspensions of the $Fe_3O_4$ particles with or without a surfactant can be used, but it is preferred to employ surfactant-free magnetic particles such as $Fe_3O_4$ in a dispersed homogeneous suspension or in a dry powder form. The microspheres of this invention can be used for administering a wide variety of therapeutic agents. The agent may be incorporated in the matrix material as a powder, if water-soluble, in the form of a water solution, or if lipid-soluble as a solution in a non-aqueous solvent. The microspheres of this invention are believed to be of particular value for administering water-soluble chemotherapeutic agents, such as anti-cancer agents whose use is now limited because of adverse side effects. Heat-labile therapeutic agents can be used such as natural products since the microcapsules can be prepared at temperatures where the therapeutic agent is stable.

A suitable process for forming the microspheres from albumin and similar matrix materials is known in the art.

For example, the procedure described by Kramer or modifications thereof can be used. See *J. Pharm. Sci.*, 63, 1646 (October 1974); and see also Scheffel et al, *J. Nucl. Med.*, 13, 498 (1972). The therapeutic agent is dissolved in a water solution of human serum albumin and emulsified with a vegetable oil. The emulsion is added with constant stirring to a larger body of the oil held at an elevated temperature. The size of the microcapsules depends on the fineness of the emulsion, and size reduction can be obtained by procedures such as homogenization or sonication. The microcapsules are heat-hardened by partial denaturation of the albumin in the hot oil. Zolle in U.S. Pat. No. 3,937,668 describes a procedure for preparing drug-containing albumin microspheres. The substance to be incorporated is mixed in the form of a powder or precipitate with the aqueous solution of albumin, which is injected into a body of oil. Hardening of such microcapsules by techniques other than denaturation of the protein are known, and include particularly treatment of the microcapsules with aqueous formaldehyde as a hardening agent. See Madan et al, *J. Pharm. Sci.*, 65, 1476 (October 1976), and U.S. Pat. Nos. 2,800,457 and 3,265,629.

In practicing the present invention, from 5 to 350 parts by weight of the magnetic particles can be employed per 100 parts of the amino acid polymer, or other carrier material. This will result in microcapsules containing corresponding proportions of the matrix material and magnetic particles. The preferred amount of magnetic material is from 10 to 150 parts by weight per 100 parts of the matrix material. The amount of the therapeutic agent can vary over a wide range, depending on the purpose for which the microspheres are to be used. However, in general, for water-soluble chemotherapeutic agents, from 1 to 20 parts by weight of the agent can be incorporated per 100 parts by weight of the matrix material. It will be understood, however, that the relative proportions of the therapeutic agent to the matrix material are not critical.

In preparing the microcapsules, an aqueous solution or dispersion of the matrix material is prepared, which can be formed into microspheres. The amount of matrix material to be used will usually be within the range from 5 to 50 parts by weight of the matrix material per 100 parts of water. With albumin and similar matrix materials preferred proportions are from 20 to 30 parts per 100 parts of water. Where a water-soluble therapeutic agent is being incorporated, it may be dissolved in the water of the matrix material solution, either before or after preparing the matrix solution.

The aqueous solution of the matrix material containing the therapeutic or diagnostic agent, either dissolved or in particulate form, is emulsified with an oil, which is preferably a vegetable oil, such as cottonseed oil, peanut oil, or the like. The aqueous phase at the time of addition of the oil will also contain the magnetic particles, which were previously added to the aqueous solution of the matrix material and dispersed therein. The proportions of the aqueous phase to the oil phase can conveniently range from about 1 to 5 parts by weight of the aqueous phase per 100 parts of the oil phase. This provides separation of the oil droplets, and prevents coalescence of the droplets in forming the microspheres. The water-in-oil emulsion is then treated to reduce the size of the dispersed droplets. Procedures such as homogenization, sonication, or both can be used. The completed emulsion should contain dispersed water phase droplets of the desired average size for the microspheres, such as less than 1.5 microns in average size. Larger or smaller microspheres can be used, such as microspheres up to 2-3 microns in average diameter, or below an average size of 1.2 microns. In general, however, the preferred size range is from about 0.5 to 1.5 microns.

The emulsion is then added to a larger body of oil, which is preferably the same oil used to form the emulsion. In practice, cottonseed oil has been found to give good results. To promote the separation of the water droplets, the emulsion can be added in small increments to the oil bath, such as by dropwise addition. Preferably, also, the addition is accompanied by rapid stirring of the oil into which the emulsion is being introduced.

Where the therapeutic agent contained in the emulsion is not heat sensitive, the oil bath into which the emulsion is introduced can be heated to a temperature at which the matrix material, such as albumin, is partially denatured and hardened. For maximum hardening, temperatures in excess of 100° C. can be used, such as temperatures ranging from about 125° to 172° C. A lesser degree of hardening and denaturation can be obtained at temperatures within the range from 50° to 100° C. Where heat-hardening is employed, no chemical treatment is needed to harden the microspheres. Most hardening, like chemical hardening, serves to delay release of the drug from the microspheres. In fact, tailor-made release rates can be achieved by studying time and temperature of hardening versus drug release.

For incorporation of water-soluble heat-labile chemotherapeutic agents in the microspheres, it has been found that the process can be carried out at essentially room temperature. The body of oil into which the emulsion is introduced can be maintained at a temperature at which there is no inactivation of the chemotherapeutic agent, such as a temperature in the range of 1° to 45° C. Usually, it will not be necessary to either heat or cool the body of oil, using an essentially ambient temperature, such as a temperature ranging from about 20° to 30° C.

It has been found that although there is no heat-denaturation of the matrix material, such as albumin, the microspheres after introduction into the oil bath will maintain morphology and integrity as separate microspheres in a nonwater miscible organic solvent, such as diethyl ether, ligroin, benzene, hexane, petroleum ether, and the like. The oil may be removed by washing with the organic solvent, such as diethyl ether, and the microspheres suspended in the organic solvent for further processing. The organic solvent can be removed by centrifugation and/or evaporation, and the resulting microcapsules dried, preferably by lyophilization. The resulting product has a relatively rapid drug release rate in water or blood, but the lyophilized microspheres if not subjected to proteolytic enzyme action will continue to retain and release a water soluble agent over periods up to 48 hours.

Where a slower release rate is desired, and particularly where greater resistance to proteolytic enzyme degradation is needed, the microspheres after being formed and before drying can be treated with a crosslinking agent for the amino acid polymer. Hardening of amino acid materials such as albumin can be accomplished, as is known in the art, by treatment with a glyoxal or aldehyde reagent. Specific reagents include dimethyl glyoxal, glyoxal, diphenyl glyoxal, formaldehyde, 2,3 butanedione, and similar aldehydes. The glyoxal or aldehyde is preferably soluble in the organic solvent used to wash the microcapsules free of oil. For example, the organic solvent can contain a concentration of 0.2% to 20% by weight of the cross-linking agent, and may be contacted with the microspheres after or during the removal of the oil for from 5 to 120 minutes, depending on the degree of cross-linking desired. In general, the greater the amount of cross-linking, the slower will be the release rate for the water-soluble chemotherapeutic agent.

After completion of the cross-linking step, the microspheres can be washed free of excess cross-linking agent with a suitable organic solvent, as described above, such as diethyl ether, the residual solvent evaporated, and the microspheres dried, such as by lyophilization.

Formaldehyde is a particularly desirable cross-linking agent, but is generally available commercially only as a water solution, such solutions contain from 4 to 37% by weight formaldehyde. Although formaldehyde is preferentially water soluble, it can be transferred to an organic solvent, such as the solvents described above, by adding a salt to the water solution. Ammonium sulfate can be used for this purpose at a concentration in the aqueous formaldehyde of about 60 to 80% by weight. The organic solvent containing the transferred formaldehyde can then be used for treating the microspheres to cross-link the matrix material.

As will be discussed in further detail and illustrated by the foregoing examples, the carrier microspheres prepared in accordance with this invention are capable of being immobilized at the rate of blood flow in capillaries while not being retained in the arteries to which they are introduced under the same magnetic field, the difference in magnetic responsiveness or retention being due to the difference in blood flow rates between arterial and capillary flow. For the purposes of the present invention, at least 90% of the microspheres should be immobilized by a magnetic induction of 8,000 gauss when an aqueous suspension of the microspheres is pumped at a rate of 0.05 cm/sec through a conduit of 0.168 cm internal diameter. However, not over 10% of the microspheres should be immobilized by the same magnetic induction when pumped through the same conduit at a flow rate of 10 cm/sec or greater. Preferably, at least 90% of the microspheres are immobilized by the described procedure at a flow rate of 0.05 cm/sec but not over 5% of the microspheres are immobilized at the flow rate of 10 cm/sec. For test purposes, the magnetic induction can be applied by a bipolar magnet with it poles equidistant from the centerline of the tube through which the suspension is being pumped, and the 8,000 gauss field is referenced to a plane intersecting the tube at right angles to the direction of flow and extending for at least 1.0 centimeters (cm) in the direction of flow. A suitable procedure is described in detail in copending application Ser. No. 032,399, filed Apr. 23, 1979.

Reference to the following examples provides further information concerning the method of this invention.

EXAMPLE I 125 mg human serum albumin, 10 mg bulk purified adriamycin HCL, and 36 mg $Fe_3O_4$ powder (200 A average particle size) was placed in a 50 ml beaker and dissolved and suspended respectively in 0.5 ml distilled water. For experimental purposes, the albumin may be trace labeled with 0.1 mg $^{125}I$-bovine-serum-albumin. The suspension was stirred well to evenly disperse the $Fe_3O_4$ in the albumin-adriamycin solution, but no surfactant was employed to aid the dispersion. Next 30 ml of cottonseed oil was added to the suspension forming a water-in-oil emulsion, which was then stirred well to disperse the aqueous phase into the oil.

The resultant emulsion was homogenized by sonication (Branson Sonifier Model 185) at 100 watts for one minute at 4° C. Next, the homogenate was added dropwise into 100 ml of cottonseed oil at 25° C. being constantly stirred at 1800 RPM for 10 minutes to fully disperse the emulsion.

The oil was then removed by washing 4 times in 60 ml diethyl ether anhydrous and centrifuged at 2000×g for 30 minutes. After the fourth wash the oil free microspheres were then hardened by a formaldehyde 1% w/v solution in 100 ml ether (8 mg microspheres/ml ether-formaldehyde solution). The ether-formaldehyde solution was prepared by transferring aqueous formaldehyde to the ether phase by shaking a 1:5 (37% aqueous formaldehyde:ether) solution in the presence of saturating ammonium sulfate. The amount of formaldehyde transferred at this ratio was determined in a separate study using tritium labeled formaldehyde (1.5 mCi/1.5 mg) as a trace label in the 37% aqueous solution. The hardening was accomplished by dispersing the washed microspheres in the formaldehyde/ether and stirring at 100 RPM for the desired time (5 min to 2 hrs), depending on the extent of hardening desired. After hardening was terminated, the formaldehyde cross-linking reagent was removed by centrifugation in ether, four times. Any remaining ether was allowed to evaporate and the resultant material was further processed by lyophilization, and then stored at 4° C.

The microcapsule product contained approximately by weight 21% $Fe_3O_4$, 73% albumin, and 6% adriamycin. Examination by immersion fixation-transmission electron microscopy confirmed that the microcapsules were generally spherical in shape and of an average size of about 1 micron.

The magnetic iron particles (P) of $Fe_3O_4$ are concentrated in the peripheral portions of the microspheres. No particle-dispersing surfactant was used in preparing these microcapsules. When the $Fe_3O_4$ is incorporated in the microcapsules in the form of an aqueous suspension containing the surfactant, the magnetic particles tend to disperse throughout the microcapsules relatively uniformly.

EXAMPLE II

The procedure for preparing the microspheres was identical to that of Example I except that 135 mg $Fe_3O_4$ was used instead of the 36 mg of Example I. The microcapsule product contained approximately by dry weight 50% $Fe_3O_4$, 4% adriamycin, and 46% albumin.

EXAMPLE III

Microcapsules were prepared by the identical procedure of Example I, using approximately the same amount of $Fe_3O_4$ as in Example II. The $Fe_3O_4$ was in the form of an aqueous suspension containing a surfactant, aqueous base Ferrofluidics $Fe_3O_4$ Catalog No. A-01, 400 gauss saturation (Ferrofluidics Corporation, Burlington, Massachusetts). 0.3 ml of the A-01 product was added, containing approximately 130–140 mg $Fe_3O_4$. The average $Fe_3O_4$ particle size was in the range of 150–200 Angstroms. The microcapsular product contained approximately by dry weight 51% $Fe_3O_4$, 4% adriamycin, and 45% albumin.

EXAMPLE IV

The procedure of Example I was followed except that the homogenate was added to 100 ml of preheated oil (135° C.) for 10 minutes. Washing is as described previously, but the aldehyde hardening is omitted. The rest of the procedure is the same.

EXAMPLE V

A. Same procedure as Example I except microspheres are not hardened by a cross-linking agent or by heat. The oil bath is at a temperature of 20°–25° C. After the oil has been washed away with diethyl ether anhydrous 4 times, the spheres are air dried, then lyophilized and stored at 4° C.

Stability of the resultant microspheres was tested as follows: First, 5 microliters of $^{125}$I-bovine serum albumin (1.51 mCi/mg) was added in the initial homogenate to trace label the microspheres. An aliquot of the resultant microspheres was then suspended and sonicated for 2 minutes in 0.154 M NaCl-0.1% Tween 80 and incubated at 37° C. for 24 and 48 hours. After this period of time, the suspension was centrifuged at 2000×g for 10 minutes and the supernatant and pellet were counted in a gamma counter. The number of counts obtained in the supernatant (after subtracting free label) was divided by the total number of counts was regarded as the percentage breakdown of the carrier (non-pelleting). Only 16% of the microspheres had deteriorated after 24 hrs. and 37% after 48 hrs. With formaldehyde or heat-hardening less than 3% deterioration occurs in 48 hrs.

B. Same procedure as Example I except 3,400 units of urokinase was added to the 125 mg of HSA omitting the $Fe_3O_4$ and adriamycin. No cross-linking was done in this experiment.

Two mg of the resultant microspheres were placed into 16 12×75 mm tubes for duplicate time course of 0, 15, 30, 60 minutes; 2, 4 and 6 hours. At the appropriate time, microspheres were suspended in sodium barbital buffer (0.05 M) and left at room temperature. Finally at zero time all tubes were centrifuged at 3,500 RPM (1900×g) for 15 minutes at 4° C. and 25 microliters of the supernatants were pipetted into appropriate wells on fibrin-agar plates. Plates were then read 4 and 6 hours later for fibrinolysis (i.e. diameters).

It was found that 60% of maximum lysis was seen after 10 minutes on fibrin-agar plate.

EXAMPLE VI

As a variation of the procedure of Example I, 2,3-butanedione (5% v/v in anhydrous ether) or butyraldehyde (10% v/v in anhydrous ether) is employed as a cross-linking agent, the contact time ranging from 5 minutes to 2 hours. The product is recovered and dried as described in Example I.

As a further variation of the procedure of Example I, 20 mg of poly-L-lysine or polyglutamic acid is combined with the 125 mg of human serum albumin. The rest of the procedure is identical. In another modification, hemoglobin is substituted on an equal weight basis for the albumin.

EXAMPLE VII

The magnetic responsiveness of the microspheres under varying liquid flow rates was studied under standardized conditions, using the apparatus and procedure described in co-pending application Ser. No. 32,399, filed Apr. 23, 1979. The comparison of trace-labeled samples of microspheres, prepared as described in Examples I and II, is summarized below in Table A. The data demonstrates that magnetic retention varies reproducibly with flow rate, and shows that over the range from 0.05 to 10 cm/sec that the retention can be varied from substantially complete to substantially no retention. For the microspheres containing 21% $Fe_3O_4$ and flowing at 0.05 cm/sec, 99% were retained, but only 0.2% at 9.8 cm/sec. The microspheres containing 50% $Fe_3O_4$ (dry weight basis) were 99% retained at 0.05 cm/sec, but only 8–10.7% retained at flow rates of 6.60–9.80 cm/sec.

Table B as set out below represents a comparison of magnetic responsiveness of the microspheres prepared in Example II with those of Example III. The microspheres are of the same size (average 1 micron diameter) and contain approximately the same amount of magnetic iron (50–51%) but the magnetic particles are differently distributed. With peripheral type distribution greater magnetic responsiveness is obtained. This makes it possible to use a lesser proportion of the magnetic particles in relation to the matrix material, permitting larger amounts of a therapeutic agent to be incorporated with the matrix material in the same size microspheres.

TABLE A

Retention of Microspheres at 8,000 Gauss

| Velocity (cm/sec) | % Retention | |
|---|---|---|
| | 21% $Fe_3O_4$ | 50% $Fe_3O_4$ |
| 0.05 | 97.0 | 99.0 |
| 0.20 | 85.3 | 98.0 |
| 0.50 | 66.5 | 94.6 |
| 0.70 | 56.2 | 91.9 |
| 1.00 | 40.1 | 78.3 |
| 1.60 | 24.2 | 66.0 |
| 2.30 | 19.2 | 51.0 |
| 3.30 | 9.6 | 40.1 |
| 5.00 | 6.1 | 16.3 |
| 6.60 | 5.3 | 8.0 |
| 9.80 | 0.2 | 10.7 |

TABLE B

Comparison Magnetic Responsiveness of Microspheres with Peripheral and Dispersed Magnetic Material (50–51% $Fe_3O_4$)

| Velocity (cm/sec) | % Retention | |
|---|---|---|
| | Dispersed | Peripheral |
| 0.05 | 99.0 | 99.3 |
| 0.20 | 98.0 | 99.5 |
| 0.50 | 94.6 | 95.4 |
| 0.70 | 91.9 | 89.9 |
| 1.00 | 78.3 | 88.1 |
| 1.60 | 66.0 | 83.1 |
| 2.30 | 51.0 | 71.0 |
| 3.30 | 40.1 | 58.0 |
| 5.00 | 16.3 | 35.6 |
| 6.60 | 8.0 | 29.1 |
| 9.80 | 10.7 | 10.4 |

EXAMPLE VIII

Microspheres containing approximately 21% $Fe_3O_4$ were prepared as described in Example I using trace labeled albumin.

The microspheres were tested in vivo. The model chosen, based on ease of manipulation and access, was the central ventral artery in the tail of the rat. The animals used were 400 gram female retired breeder rats.

The artery was partially exposed at the base of the tail and a polyethylene catheter presoaked in a 0.6% heparin 1000 in saline solution was inserted caudally 4 cm. A permanent bipolar magnet with a field strength of 8000 Oe was placed 7 cm caudally from the point of insertion of the catheter. Varying amounts of microspheres, suspended in 0.1% Tween 80 in 0.9% NaCl, were infused by a constant flow syringe pump (Sage, Model 341) at 0.06 ml/min which corresponds to the blood flow rate of this artery previously determined. After infusion the catheter was removed and the magnet was retained in position for thirty minutes. A transcuataneous Doppler apparatus (Parks Electronics Lab, Model 881-A) was used to verify resumption of blood flow following removal of the catheter from the artery. After the thirty minute period, the rat was sacrificed via intracardiac injection of saturated KCl and the organs were removed and counted for $^{125}I$ activity in a Packard (Model 578) gamma counter. The tail was cut into four equal sections, and each section was counted individually. Results of this study are shown in Table C. Multiple animals for each field strength were used to determine the average $^{125}I$-magnetic-microsphere body distribution.

In a modification of the foregoing procedure, the animals were sacrificed 24 hours after removing the tail from the magnetic field. Once again, 50% of the injected counts were found at the target site. This phenomenon, as well as the carrier distribution in the skin, suggests the possibility that the carrier is lodging in the vascular endothelium or possibly traversing the vascular basement membrane into interstitial tissue due to the magnetic force applied. This phenomenon would be extremely desirable as the microspheres would act as extra vascular depots releasing the drug at a fixed rate at a desired target site.

An additional animal model was chosen to illustrate carrier localization. In this study the carrier was localized to the lungs of $BDF_1$ female mice. A modification of the above procedure for introduction of the carrier consisted of tail vein injection rather than catheterization, and the use of a unipolar magnet instead of a bipolar to generate the field. Thirty minutes following injection, the mouse was sacrificed and the organs counted for $^{125}I$ activity as described above. In the experimental animals, 45–50% of the total counts injected were found in the lung as compared to 6–12% of the counts found in control animal lungs.

TABLE C

| MAGNETIC FIELD GAUSS | Average Percent Distribution of $^{125}I$-Magnetic Microspheres | | | | | | | | |
|---|---|---|---|---|---|---|---|---|---|
| | TAIL SECTION | | | | ORGAN | | | | |
| | 1 | 2 | 3 | 4 | Liver | Spleen | Kidney | lung | Heart |
| No Field | 0 | 0 | 0 | 0 | 80 | 10 | <1 | 10 | 0 |
| 4000 | 0 | 0 | 3 | 0 | 85 | 7 | <1 | 5 | 0 |
| 6000 | 0 | 0 | 19 | — | 57 | 8 | <1 | 12 | 0 |
| 8000 | 0 | 1 | 50 | 0 | 39 | 4 | <1 | 7 | 0 |

EXAMPLE IX

As previously stated, the intravascularly-administrable, magnetically-localizable biodegradable carrier of this invention can be used for administering a wide variety of therapeutic agents. The carrier is of particular value for administering those therapeutic agents which have high toxicity or undesirable side effects when administered parenterally to the whole body. By the use of the localizable carriers of this invention, a far smaller amount of the active therapeutic agent can be employed with equivalent therapeutic effects since substantially the entire amount of drug administered is localized within the particular body area, be it a tumor site or an inflamed joint. The carrier of this invention is particularly useful in administering water soluble oncolytic agents which are known to be toxic or to have undesirable side effects. The highly toxic oncolytic agents are greatly restricted in use because of their toxicity, but with other oncolytic agents while the toxicity is not so great and the patient can survive a course of treatment, the accompanying side effects are undesirable. Administering the agent in a carrier of this invention would then be more a matter of choice with a view toward the patient's well being in avoiding this particular side effect.

The use of the carrier of this invention in administering the toxic oncolytic agent, adriamycin (doxorubicin), illustrates the advantageous nature of our novel carrier and of its use in the treatment of neoplasms. In this experiment, magnetic microspheres prepared by the procedures set forth herein having adriamycin dispersed therein were used to treat transplanted subcutaneous solid Yoshida sarcoma tumors as follows:

Magnetic microspheres (average 1 μm in diameter) were prepared by using a phase emulsion polymerization process in which the aqueous phase consisted of human serum albumin, adriamycin and magnetite ($Fe_3O_4$). One hundred twenty-five mg. of human serum albumin, 16 mg. of adriamycin and 36 mg. of magnetite were combined in 0.5 ml. distilled water.

To this mixture were added 30 ml. of cottonseed oil and the emulsion was homogenized by sonication with a sonifier having a recirculating attachment probe for one minute at 100 watts. The resultant homogenate was added dropwise to 100 ml. of continuously stirred cottonseed oil preheated to 125° C. The temperature was maintained by immersion of the reaction vessel in a constant temperature oil bath. After ten minutes, the suspension was removed from the heating bath, cooled to 25° C. and washed four times with anhydrous diethyl ether. The resulting microspheres were stored under ether at 4° until use. The encapsulation procedure resulted in 97% biologically active adriamycin. Control "placebo" microspheres were prepared in an identical fashion.

The ascitic form of the Yoshida rat sarcoma was serially passaged intraperitoneally in Holtzman rats (200–270 gms.). Six to eight days before drug administration, animals were inoculated with $3.5 \times 10^8$ cells subcutaneously into the lateral aspect of the tail, resulting in solid tumor nodules. At the time of drug administration, tumors were both visible and measurable, and, on occasion, the skin overlying the tumor was necrotic. Average tumor size was $9 \times 45$ mm; however, tumors up to 60 mm in length were used.

The experimental protocol required a double blind study. Animals were therefore color coded prior to use and randomly chosen. Workers treating the animals recorded the mode of therapy initiated. Other investigators assessed tumor growth. In both treated and control groups, animals received only single dose treatment 6–8 days post-inoculation.

For drug administration, animals were anesthetized with methoxyflurane and the ventral caudal artery was partially exposed at the base of the tail. A polyethylene catheter presoaked in a solution of 0.6% heparin 1000 in saline was inserted caudally to a point 2 cm away from the proximal margin of the tumor. A permanent bi-polar magnet with a field strength of 5500 Oe and a gap of 10 mm was positioned so that the tumor was adjacent to a pole face. The microspheres, suspended in 1 ml. of 0.154 N saline containing 0.196 Tween 80, were infused by a constant flow syringe pump at 0.5 ml./min. Following infusion of the microspheres, a bolus of 1 ml. normal saline was infused at the same rate.

Microspheres were administered to three animal groups consisting of 10–12 rats each. Twelve animals received microspheres at a dosage of 0.5 mg./kg. of adriamycin while the tumor was exposed to the magnetic field. Ten animals received "placebo" microspheres (without drug) infused in the identical manner with similar exposure of the tumor to the magnetic field. A third group received drug-bearing microspheres, but without the application of a magnetic field. In a positive control group, adriamycin was administered IA (via caudal artery) at 0.5 mg./kg. and 5 mg./kg., and I.V. at 5 mg./kg.

The magnet was retained in position for 30 minutes after which it was removed and the catheter withdrawn. The skin overlying the cut-down site was sutured and animals were observed for weight change, size of tumor, and death. Surviving animals were sacrificed 29 days after treatment. Organs were examined both grossly and microscopically for evidence of tumor or distant metastases.

Results of single dose therapy with adriamycin are presented in Table D. Tumor size increased markedly in all animals treated with single dose systemic adriamycin regardless of the route or mode of administration, or dose (0.5 mg./kg. versus 5 mg./kg.). Control animals receiving either no treatment or placebo microspheres also demonstrated a significant increase in tumor size. In contrast, when microspheres containing 0.5 mg./kg. drug were infused with the presence of the magnet adjacent to the tumor, there was a significant (83%) decrease in tumor size. The weights of all animals increased during the course of the experiments with some of the weight gain attributable to the massive tumor growth in the animals. Animals receiving targeted therapy via magnetic microspheres showed no decrease in weight attributable to adriamycin toxicity.

In all groups of animals receiving either systemic adriamycin or no treatment at all, there was an 80–100% mortality rate and an 8–100% incidence of distant metastases during the 29 days the animals were observed. In contrast, no deaths or metastases occurred in animals treated with the single dose of magnetically-targeted microspheres containing adriamycin. Moreover, 75% of the animals in this group had complete tumor remission. An additional 17% had significant tumor regression. In comparison, there were no remissions or regressions in any experimental control group with the exception of a slight decrease in tumor size in one animal from the untreated control group.

TABLE D
EFFECT OF MAGNETIC MICROSPHERES CONTAINING ADRIAMYCIN ON TUMOR GROWTH IN YOSHIDA RAT SARCOMA

| | GROUP A UNTREATED CONTROLS | GROUP B ADM SPHERES (MAGNET) 0.5 mg/kg IA | GROUP C ADM SPHERES (NO MAGNET) 0.5 mg/kg IA | GROUP D ADM SOL. (NO SPHERES) 0.5 mg/kg IA | GROUP E ADM SOL. (NO SPHERES) 5 mg/kg IA |
|---|---|---|---|---|---|
| Init. Tumor Size | 36.2 | 28.7 | 27.8 | 25.7 | 26.8 |
| Final Tumor Size | 46.4 | 5.0 | 48.5 | 44.5 | 41.9 |
| Tumor Change | +28% | −83% | +74% | +73% | +56% |

The new oncolytic agent, vindesine (23-amino-4-desacetoxy-23-demethoxy-4-hydroxyvincaleucoblastine sulfate)—see papers presented at the Vindesine International Work Shop at Frankfurt, Germany, July 7, 1978, appearing in *Cancer Chemotherapy and Pharmacology*, 2, 229–274 (1979) and references appearing therein—has also been coacervated in magnetite-containing albumin microspheres by the above procedure to yield magnetically-localizable microspheres containing 6% by weight of vindesine sulfate. This formulation can be used in the treatment of vindesine-susceptible tumors which have a blood supply from essentially a single artery. Such vindesine-containing microspheres can also be used in experimental animals having transplanted tumors susceptible to vindesine treatment. Other oncolytic agents which can be incorporated into our novel microspheres include methotrexate, fluorouracil, 6-mercaptopurine, vinblastine, vincristine, mitomycin C, actinomycin D, daunorubicin, bleomycin and mithramycin.

Tumors which can best be treated by the use of magnetically-localizable microspheres of this invention include tumors of the head and neck, of the female genital track and of the bladder. Not all tumors occurring in these sites may be treatable by the procedure of this invention since susceptible tumors must have both an arterial blood supply and a vascular system such that the magnet can draw the magnetic microspheres from the artery into the capillaries and from the capillary bed, into the tumor.

We claim:

1. The method of delivering a therapeutic agent to a target site associated with a capillary bed of the body, comprising the steps of:
   (a) incorporating the therapeutic agent in microspheres formed from a biodegradable matrix material with magnetic particles embedded therein, said magnetic particles having an average size of not over 300 Angstroms, said microspheres having an average size of less than 1.5 microns and passing into said capillary bed with the blood flowing therethrough;
   (b) introducing said therapeutic agent-containing microspheres into an artery upstream of said capillary bed;
   (c) applying a magnetic field to the area of the body of said capillary bed and artery, said magnetic field being of a strength capable of immobilizing said microspheres at the blood flow rate of said capillary bed while permitting said microspheres to pass through said artery at the blood flow rate therein;
   (d) immobilizing at least part of said microspheres in capillaries of said target bed by said magnetic field application while blood continues to perfuse therethrough; and (e) removing said magnetic field before said therapeutic agent is released, said microspheres being retained in said capillary bed after said removal of said magnetic field for release of said therapeutic agent in effective therapeutic relation to said target site.

2. The method of claim 1 in which said microspheres have an average size within the range from 0.5 to 1.5 microns.

3. The method of claim 1 or claim 2 in which said matrix material is human serum albumin.

4. The method of delivering a watersoluble anti-cancer agent to a target capillary bed of the body associated with a tumor, comprising the steps of:
(a) incorporating the water-soluble anti-cancer agent in microspheres formed from a biodegradable matrix material with magnetic particles embedded therein, said magnetic particles having an average size of not over 300 Angstroms, said microspheres having an average size of less than 1.5 microns and passing into said capillary bed with the blood flowing therethrough, said microspheres containing from 10 to 150 parts by weight of said magnetic particles per 100 parts of said matrix material;
(b) introducing said anit-cancer agent containing microspheres into an artery upstream of said capillary bed;
(c) applying a magnetic field to the area of the body of said capillary bed and artery, said magnetic field being of a strength capable of immobilizing said microspheres at the blood flow rate of said capillary bed while permitting said microspheres to pass through said artery at the blood flow rate therein;
(d) immobilizing at least part of said microspheres in capillaries of said target bed by said magnetic field application while blood continues to perfuse therethrough; and
(e) removing said magnetic field before said anti-cancer agent is released from said microspheres, said microspheres being retained in said capillary bed after said removal of said magnetic field for release of said anti-cancer agent in effective therapeutic relation to said tumor.

5. The method of claim 4 in which said agent is adriamycin.

6. The method of claim 4 or claim 5 in which said matrix material is *human serum* albumin.

7. The method of claim 4 in which said amino acid polymer is human serum albumin, and in which said anti-cancer agent is adriamycin.

8. The method of claim 4 in which said microspheres have an average size within the range from 0.5 to 1.5 microns.

9. The method of claim 4 or claim 8 in which said microspheres have an average size of not over 1.2 microns.

10. The method of delivering a water-soluble anti-cancer agent to a target capillary bed of the body, comprising the steps of:
(a) incorporating the water-soluble anti-cancer agent in microspheres formed from human serum albumin with magnetic particles embedded therein, said magnetic particles having an average size of not over 300 Angstroms, said microspheres having an average size within the range from 0.5 to 1.5 microns and passing into said capillary bed with the blood flowing therethrough, said microspheres containing from 10 to 150 parts by weight of said magnetic particles per 100 parts of said albumin;
(b) introducing said anti-cancer agent containing microspheres into an artery upstream of said capillary bed;
(c) applying a magnetic field to the area of the body of said capillary bed and artery, said magnetic field being of a strength capable of immobilizing said microspheres at the blood flow rate of said capillary bed while permitting said microspheres to pass through said artery at the blood flow rate therein;
(d) immobilizing at least part of said microspheres in capillaries of said target bed by said magnetic field application while blood continues to perfuse therethrough; and
(e) removing said magnetic field before said anticancer agent is released from said microspheres, said microspheres being retained in said capillary bed after said removal of said magnetic field for release of said anti-cancer agent in effective therapeutic relation to said tumor.

11. The method of claim 10 in which said microspheres have an average size of not over 1.2 microns.

12. The method of claim 10 or claim 11 in which said magnetic field is maintained substantially at the same strength from its application to its removal.

* * * * *